United States Patent [19]

Babler

[11] Patent Number: 4,916,250
[45] Date of Patent: Apr. 10, 1990

[54] PHOSPHONATE REAGENT COMPOSITIONS

[75] Inventor: James H. Babler, Chicago, Ill.

[73] Assignee: Loyola University of Chicago, Chicago, Ill.

[21] Appl. No.: 264,543

[22] Filed: Oct. 31, 1988

[51] Int. Cl.$^4$ .............................................. C07F 9/40
[52] U.S. Cl. ...................... 558/217; 558/87; 558/88; 585/351; 560/128; 562/510
[58] Field of Search .................................. 558/217

[56] References Cited

U.S. PATENT DOCUMENTS 3,600,473  8/1971  Sarmatis ............................. 558/217
4,175,204  11/1979  Babler ................................ 560/262

OTHER PUBLICATIONS

Bourguignon, J. J. and C. G. Wermuth, "Lactone Chemistry. Synthesis of Beta-Substituted, Gamma-Functionalized Butanolides and Butenolides and Succinaldehydic Acids from Glyoxylic Acid", *J. Org. Chem.* (1981), 46, pp. 4889–4894.

Czekanski, T., H. Gross and B. Contisella, "Methandiphosphonsaureester durch UV-Induzierte Michaelis-Becker-Reaktion", 35, *J. f. prakt. Chemie.* Band 324, Heft 4 (1982), pp. 537–544.

Curley, R. W., Jr. and C. J. Ticoras, "Stereospecific Synthesis of the Important Retinoid Synthon Ethyl trans-3-Formyl-2-butenoate via Direct Two-Stage Oxidation of Ethyl 3-Methyl-2-butenoate", *J. Org. Chem.* (1986), 51, pp. 256–258.

Isler, O., W. Huber, A. Ronco and M. Kofler, "Synthese des Vitamin A", *Helv. Chim. Acta*, 30, 1947, vol. XXX, pp. 1911–1927.

Julia, M. and D. Arnould, "Synthese a l'aide de Sulfones, III Syntheses de la vitamine A", *Bull. Soc. Chim. Fr.* (1973), Part 2, pp. 746–750.

Laugraud, S., A. Guingant and J. d'Angelo, "A Direct Route for the Synthesis of (E)-3-Alkyl-4-Oxo-2-butenoic Acid Esters", *J. Org. Chem.* (1987), 52, pp. 4788–4790.

Liu, R. S. H. and A. E. Asato, Tetrahedron Report No. 165, "Photochemistry and Synthesis of Stereoisomers of Vitamin A", *Tetrahedron*, vol. 40, No. 11 (1984), pp. 1931–1969.

Pattenden, G. and B. C. L. Weedon, "Carotenoids and Related Compounds. Part XVIII, Synthesis of Cis and D-Cis-Polyenes by Reactions of the Wittig Type", *J. Chem. Soc.* (C) (1968), pp. 1984–1997.

Pommer, H. and R. Kuhn, "Synthesen in der Carotinoid-Reihe", *Angew. Chem.*, 72 (1960), No. 23, pp. 911–915.

Rammamurthy, V., G. Tustin, C. C. Yau and R. S. H. Liu, "Preparation of Sterically Hindered Geometric Isomers of 7-Cis-Beta-Ionyl and Beta-Ionylidene Derivatives in the Vitamin A Series", *Tetrahedron*, vol. 31 (1975), pp. 193–199.

Reif, W. and H. Grassner, "Die Technische Vitamin-A-Synthese der BASF", *Chemie-Ing.-Techn.*, 45 (1973)m No. 10a, pp. 646–652.

Rosenberger, M., W. Jackson and G. Saucy, "The Synthesis of Beta, Gama and Alpha, Beta-Unsaturated Aldehydes via Polyene Epoxides", *Helvetica Chimica Acta*, vol. 63, Fasc. 6 (1980), No. 175, pp. 1665–1674.

Surmatis, J. D. and R. Thommen, "The Synthesis of Trans-Beta-Carotene from Retinyl Phosphonate by the Michaelis-Arbuzov Reaction", *J. Org. Chem.*, vol. 34, No. 3 (1969), pp. 559–560.

*Primary Examiner*—Anton H. Sutto
*Attorney, Agent, or Firm*—Marshall, O'Toole, Gerstein, Murray & Bicknell

[57] ABSTRACT

Novel phosphonate compounds of the formula

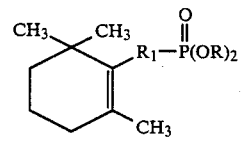

are disclosed and claimed, as well as methods for manufacturing the phosphonates from C-14 through C-16 aldehydes. The phosphonate compounds of the present invention can be employed to form 13-cis retinoic acid, retin-A and beta-carotene.

8 Claims, No Drawings

PHOSPHONATE REAGENT COMPOSITIONS

BACKGROUND OF THE INVENTION

The present invention relates to novel phosphonates which can be employed as precursors to a variety of biologically-active materials; including 13-bis retinoic acid (accutane), retin-A and beta carotene. The phosphonates of the present invention can be synthesized by the reaction of a cyclohexenyl-group-containing C-14 through C-16 aldehyde, such as 2-methyl-4-(2,6,6-trimethyl-1-cyclohexen-1-yl)-2-butenal, with a phosphonic acid ester, such as methylenebisphosphonic acid, tetraethyl ester.

A procedure for producing vitamin A acetate from beta-ionone has been described by Reif and Grassner [*Chemie-Ing. Techn.*, 45, 646–652 (1973)]:

carotene from the same beta-ionone-derived triphenylphosphonium salt:

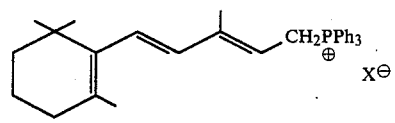

formed in the course of the Reif, et al. synthesis. The disadvantages of these procedures include the fact that the triphenylphosphine reactant required for the syntheses is relatively expensive and that the byproduct of the reactions, $Ph_3PO$, is not water soluble, thus making it difficult to isolate the desired product.

Surmatis and Thommen have described a process for preparing beta-carotene utilizing a phosphonate in a Wittig-type reaction [*J. Org. Chem.*, 34, 559 (1969)]. An essential step of this procedure involves the reaction of a C-20 dibromo compound with a trialkyl phosphite:

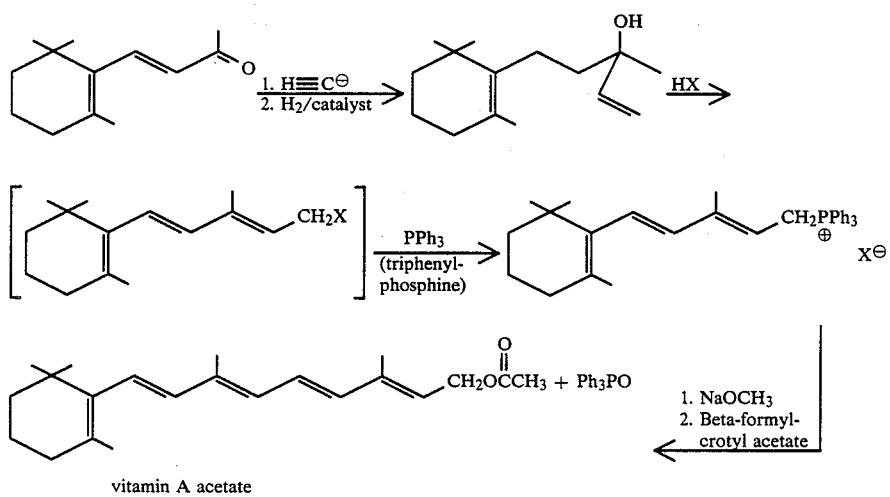

Similarly, Pommer and Kuhn [*Angew. Chem.*, 72, 911 (1960)] have described a procedure for preparing beta-

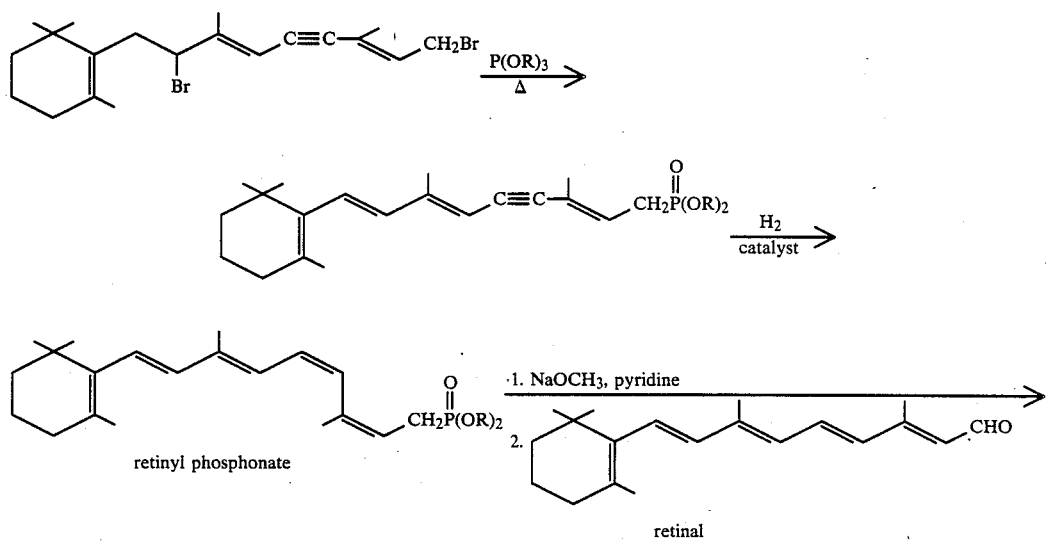

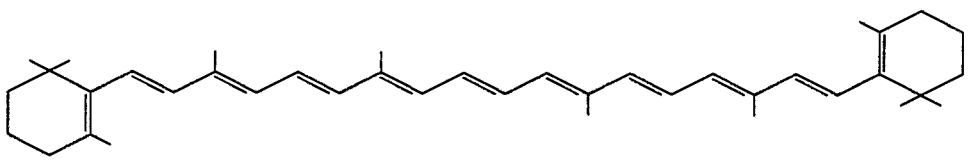

beta-carotene

Although the C-20 dibromo compound of Surmatis, et al. can be reacted with trialkyl phosphites, the literature does not report similar reactions for structurally related C-15 halides. Indeed, the literature shows that the compound 1-bromo-3-methyl-5-(2,6,6-trimethyl-1-cyclohexen-1-yl)-2,4-pentadiene

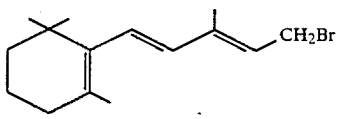

is not stable at room temperature. [*Bull. Soc. Chim. Fr.*, Part II, 746–50 (1973)].

Other procedures for preparing retinoid intermediates and beta-carotene are shown in the prior art, e.g., Babler U.S. Pat. No. 4,175,204; F. Frickel, "The Retinoids", edited by M. B. Sporn, A. B. Roberts and D. S. Goodman, Academic Press (Orlando, Fla., 1984), pp. 77–145; and R. S. H. Liu and A. E. Asato, *Tetrahedron*, 40, 1931–1969 (1984).

SUMMARY OF THE INVENTION

The novel phosphonate compounds of the present invention have the structural formula:

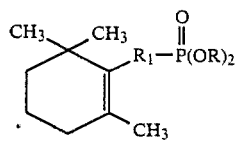

in which R is an alkyl group having up to four carbon atoms, and $R_1$ is a 3-alkyl pentadienyl group wherein the alkyl group at the 3 position is methyl, ethyl or propyl. The two double bonds in the 3-alkyl pentadienyl group, $R_1$, can be in the 1,3 or 2,4 positions (conjugated) or in the 1,4 positions (non-conjugated).

The compounds of the present invention are systematically named as esters of an alkenylphosphonic acid. Thus, for example, when $R_1$ is:

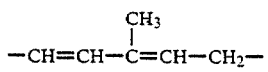

and R is ethyl, the compound is named 3-methyl-5-(2,6,6-trimethyl-1-cyclohexen-1-yl)-2,4-pentadienylphosphonic acid, diethyl ester. When $R_1$ is:

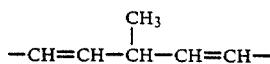

and R is isopropyl, the compound is named 3-methyl-5-(2,6,6-trimethyl-1-cyclohexen-1-yl)-1,4-pentadienylphosphonic acid, diisopropyl ester.

Other compounds within the scope of the present invention include:

3-methyl-5-(2,6,6-trimethyl-1-cyclohexen-1-yl)-1,3-pentadienylphosphonic acid, diethyl ester;

3-ethyl-5-(2,6,6-trimethyl-1-cyclohexen-1-yl)-2,4-pentadienylphosphonic acid, diethyl ester;

3-methyl-5-(2,6,6-trimethyl-1-cyclohexen-1-yl)-2,4-pentadienylphosphonic acid, dimethyl ester;

3-methyl-5-(2,6,6-trimethyl-1-cyclohexen-1-yl)-2,4-pentadienylphosphonic acid, dipropyl ester;

3-methyl-5-(2,6,6-trimethyl-1-cyclohexen-1-yl)-2,4-pentadienylphosphonic acid, dibutyl ester;

3-propyl-5-(2,6,6-trimethyl-1-cyclohexen-1-yl)-1,3-pentadienylphosphonic acid, diethyl ester; and 3-methyl-5-(2,6,6-trimethyl-1-cyclohexen-1-yl)-2,4-pentadienylphosphonic acid, diisopropyl ester.

Because of their ability to form known biologically-active compounds, dialkyl esters of 3-methyl-5-(2,6,6-trimethyl-1-cyclohexen-1-yl)-2,4-pentadienylphosphonic acid, are especially preferred.

The compounds of the present invention can be formed by the base-promoted reaction of a C-14 through C-16 aldehyde having the structure

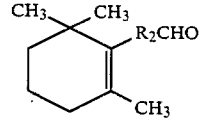

wherein $R_2$ is

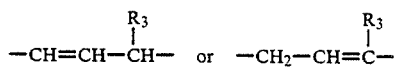

and $R_3$ is methyl, ethyl or propyl, with a methylenebisphosphonic acid ester having the structure:

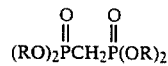

wherein each R, which can be the same or different, is selected from the class consisting of alkyl groups having up to four carbon atoms. The preferred aldehydes are C-14 materials which are derived from beta-ionone. At room temperature, reaction of the aldehyde and bis-phosphonate ester proceeds rapidly (<30 minutes) in an organic solvent containing one equivalent of a base (e.g., a Group I metal alkoxide or sodium hydride):

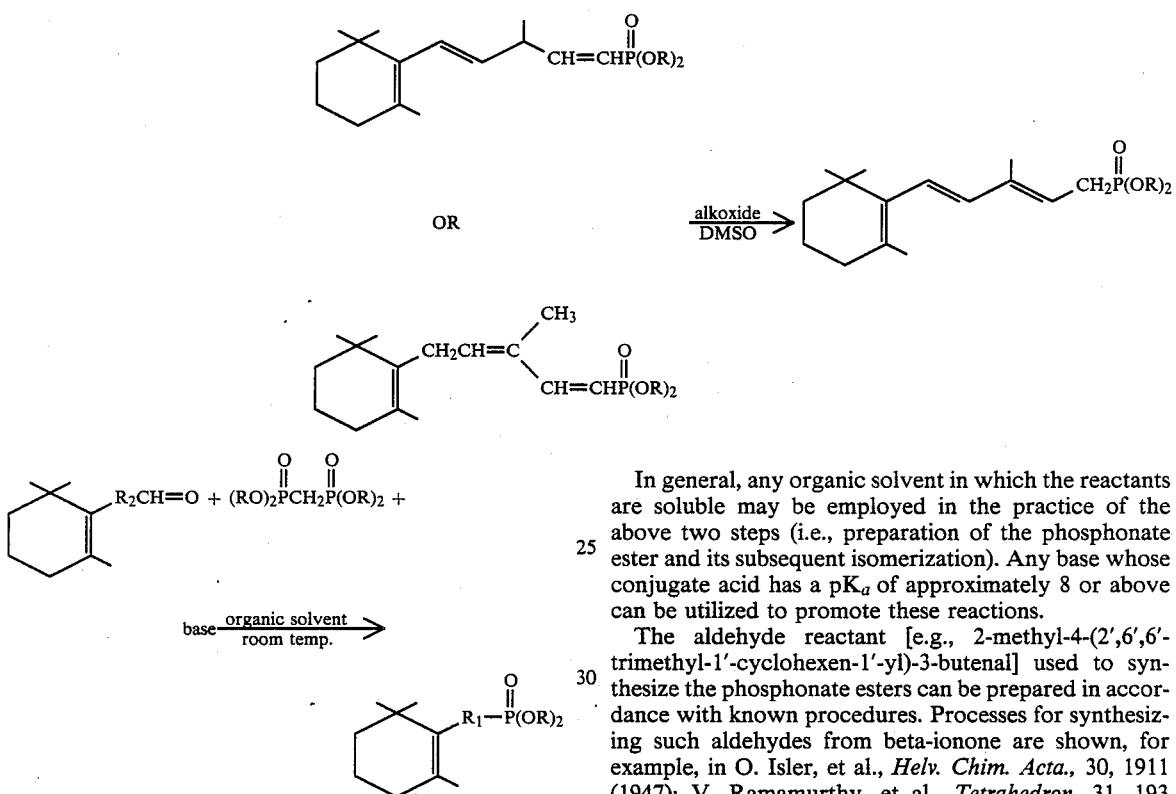

KOC(CH$_3$)$_3$, NaOCH$_3$, or NaOCH$_2$CH$_3$ with an organic solvent such as dimethyl sulfoxide (DMSO).

wherein R$_1$ is a 3-alkyl pentadienyl group, as defined above, and R is a C-1 to C-4 alkyl group. The phosphonate ester product is soluble in a variety of organic solvents and can be isolated from the reaction mixture by conventional techniques. Yields are typically in excess of 90%.

A variety of organic solvents, both polar and nonpolar, can be employed in the foregoing reaction, including hydrocarbons such as benzene, hexane, cyclohexane, and toluene; ethers such as tetrahydrofuran and diethyl ether; ethyl alcohol; polar solvents such as dimethylformamide and dimethyl sulfoxide; or mixtures of such organic solvents. Suitable bases include sodium hydride, Group I metal alkoxides, and alkali metal carbonates.

As noted previously, the double bonds in the pentadienyl moiety can be in the 1,3-; 1,4- or 2,4-positions. The 1,3- and 1,4-compounds can be isomerized to the preferred 2,4-pentadienyl phosphonates by employing a base catalyst such as an alkoxide of a Group I metal, i.e., In general, any organic solvent in which the reactants are soluble may be employed in the practice of the above two steps (i.e., preparation of the phosphonate ester and its subsequent isomerization). Any base whose conjugate acid has a pK$_a$ of approximately 8 or above can be utilized to promote these reactions.

The aldehyde reactant [e.g., 2-methyl-4-(2',6',6'-trimethyl-1'-cyclohexen-1'-yl)-3-butenal] used to synthesize the phosphonate esters can be prepared in accordance with known procedures. Processes for synthesizing such aldehydes from beta-ionone are shown, for example, in O. Isler, et al., *Helv. Chim. Acta.*, 30, 1911 (1947); V. Ramamurthy, et al., *Tetrahedron*, 31, 193 (1975); or M. Rosenberger, et al., *Helv. Chim. Acta*, 63, 1665 (1980).

The methylenebisphosphonic acid ester reactant can be prepared by reacting methylene bromide with a trialkyl phosphite [P(OR)$_3$] in accordance with the procedure shown in B. Costisella, *J. fur prakt. Chemie*, 324, 537 (1982), e.g.,

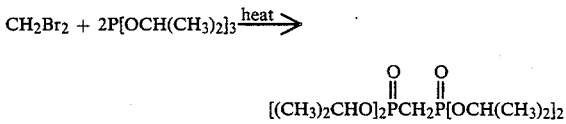

methylenebisphosphonic acid, tetraisopropyl ester, 73% yield.

The compounds of the present invention can be used in the synthesis of retinoids or beta-carotene. Illustrative examples of three such syntheses employing the novel phosphonate compounds are as follows:

Synthesis of all-trans-retinoic acid (retin-A)

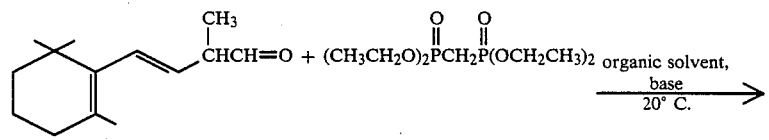

2-methyl-4-(2',6',6'-trimethyl-1'-cyclohexen-1'-yl)-3-butenal methylenebisphosphonic acid/tetraethyl ester -continued
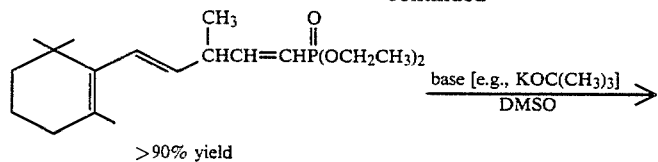
>90% yield
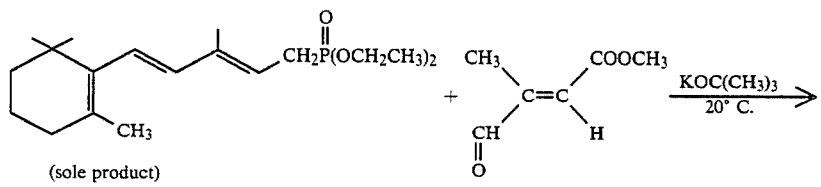
(sole product)
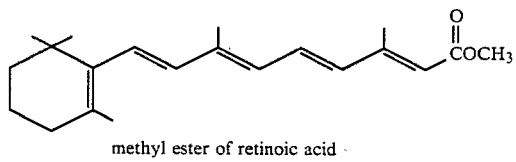
methyl ester of retinoic acid
Synthesis of 13-cis-retinoic acid (Accutane)
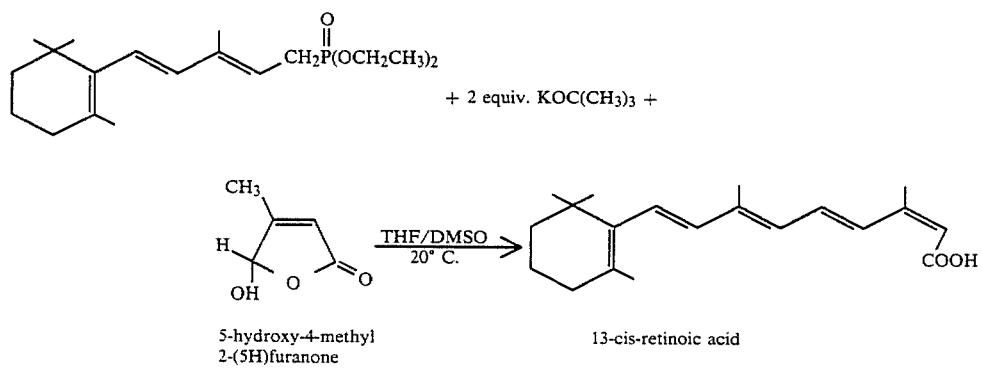
5-hydroxy-4-methyl 2-(5H)furanone
13-cis-retinoic acid
Synthesis of beta-carotene
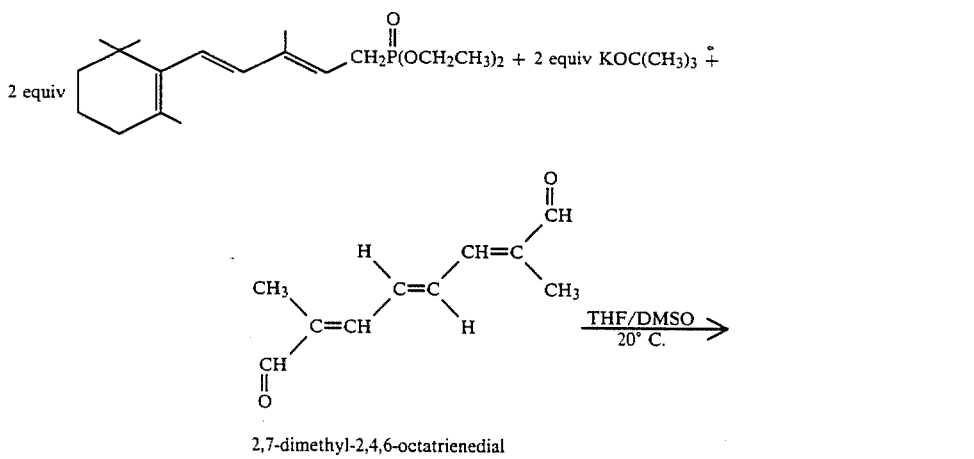
2,7-dimethyl-2,4,6-octatrienedial
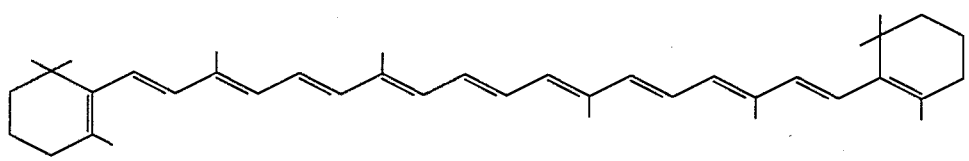
B-carotene (>60% yield)

DETAILED DESCRIPTION OF THE INVENTION

The following examples illustrate in greater detail the practice of the present invention, specifically: (i) the preparation of intermediates which can be utilized to form the phosphonate compounds of the present invention (Examples I-V); (ii) the preparation of representative novel phosphonate compounds (Examples VI-XI); (iii) the preparation of intermediates which can be reacted with the compounds of the present invention to form biologically-active materials (Examples XII-XIV); and, (iv) the preparation of biologically-active compounds utilizing the novel phosphonate compounds of the invention (Examples XV-XVII).

EXAMPLE I

Preparation of Methylenebisphosphonic Acid, Tetraethyl Ester

In accordance with a procedure suggested by H. Gross, et al., *Journal fur prakt. Chemie*, 324, 537 (1982), a mixture of 4.00 ml (57.0 mmoles) of dibromomethane and 30 mL (175 mmoles) of triethyl phosphite was gradually warmed to 90° C. over a period of 15 minutes. After maintaining the temperature at 90° C. for an additional 10 minutes, the solution was warmed to 140° C. and kept at that temperature for 2 hours. At that point, the mixture was warmed to 160° C. (external bath temperature) and heated at that temperature for an additional 15 hours, during which time ethyl bromide was slowly distilled out of the reaction mixture. Next, excess triethyl phosphite was distilled from the reaction flask, followed by distillative removal of minor amounts of ethylphosphonic acid, diethyl ester. The desired product was then obtained by distillation under reduced pressure, affording 9.03 g (55% yield) of bisphosphonate: bp 145°-160° C. (bath temperature, 0.25 mm). H. Gross, et. al., reported a 70% yield of the same compound, prepared on a larger scale (150 mmoles of dibromomethane).

EXAMPLE II

Preparation of Methylenebisphosphonic Acid, Tetraisopropyl Ester

A mixture of 1.00 ml (14.25 mmoles) of dibromomethane and 11.0 mL (44.5 mmoles) of triisopropyl phosphite was heated in the same manner as described in the procedure of Example I. Removal of excess triisopropyl phosphite, followed by a minor amount of isopropylphosphonic acid, diisopropyl ester, by distillation at reduced pressure, and subsequent evaporative distillation [bath temperature: 138°-152° C. (0.25 mm)] afforded 3.57 g (73% yield) of the desired bisphosphonate.

EXAMPLE III

Preparation of 2-Methyl-2-[2-(2,6,6-trimethyl-1-cyclohexen-1-yl)ethenyl]oxirane

A mixture of 762 mg (19.1 mmoles) of sodium hydride (60% dispersion in mineral oil, which was removed by washing with hexane prior to the addition of DMSO) and 6.0 mL of anhydrous dimethyl sulfoxide (DMSO) was heated, protected from atmospheric moisture, at a bath temperature of 65° C. for approximately 45 minutes—until evolution of hydrogen had ceased. After cooling this mixture to room temperature, it was added dropwise over a period of 10 minutes to a stirred slurry of 3.954 g (19.38 mmoles) of trimethylsulfonium iodide in 12.0 mL of 1:1 (v/v) anhydrous DMSO:tetrahydrofuran, protected from atmospheric moisture and kept cold in an ice-brine bath at approximately −5° C. The resulting gray suspension was stirred for an additional 5 minutes, after which a solution of 1.42 g (7.38 mmoles) of beta-ionone in 3.00 mL of anhydrous tetrahydrofuran was added dropwise rapidly. This mixture was subsequently stirred at approximately 0° C. for 2 hours, after which it was allowed to warm to room temperature. The product was isolated, after addition of 1 mL of water to quench the reaction, by dilution of the mixture with 50 mL of pentane and 100 mL of 10% aqueous sodium chloride. Separation of the layers was followed by washing the organic layer with 10% aqueous sodium chloride (2×100 mL), water (1×100 mL), and saturated brine (1×100 mL) in successive order. The organic extracts were then dried over anhydrous sodium sulfate and subsequently filtered. Removal of the pentane and tetrahydrofuran by evaporation at reduced pressure afforded 1.52 g (100% yield) of the desired epoxide.

EXAMPLE IV

Preparation of 2-Methyl-4-(2,6,6-trimethyl-1-cyclohexen-1-yl)-3-butenal

A solution of 1.502 g (7.28 mmoles) of the epoxide, prepared as described in Example III, in 6.00 mL of anhydrous ether was added dropwise over 5 minutes to a stirred suspension of magnesium bromide [prepared in situ from 355 mg (1.88 mmoles) of 1,2-dibromoethane and 48 mg (1.98 milli-g-atoms) of magnesium turnings] in 3.00 mL of anhydrous ether, protected from atmospheric moisture, at −10° C. The resulting mixture was stirred at −10° C. for an additional 5 minutes, after which it was diluted with 20 mL of solvent ether. The organic layer was washed in successive order with 15 mL portions of water and saturated brine, after which it was dried over anhydrous sodium sulfate and subsequently filtered. Removal of the ether by evaporation at reduced pressure afforded 1.40 g (93% yield) of the desired aldehyde, whose structure was verified by NMR analysis [δ 9.69, doublet, J=1.8 Hz, CHO; δ 1.25, doublet, J=7 Hz, CHCH$_3$]. The procedure used in Examples III and IV was developed by M. Rosenberger, et al. [*Helv. Chim. Acta.*, 63, 1665 (1980)]. An alternate route to this same aldehyde can be found in O. Isler, et al., *Helv. Chim. Acta.*, 30, 1911 (1947), subsequently modified by R. S. H. Liu, et al., *Tetrahedron*, 31, 193 (1975).

EXAMPLE V

Preparation of 2-Methyl-4-(2,6,6-trimethyl-1-cyclohexen-1-yl)-2-butenal

A mixture of 920 mg (4.46 mmoles) of the aldehyde prepared as described in Example IV and 45 mg of potassium hydroxide pellets in 3.0 mL of methyl alcohol containing 0.05 mL of water was stirred, protected from atmospheric moisture, at 20° C. for 35 minutes. The product was isolated after dilution of the mixture with 30 mL of 1:1 (v/v) pentane:ether and subsequent washing of the organic layer with 25 mL portions of 10% aqueous sodium chloride and saturated brine. Drying of the organic extracts over anhydrous magnesium sulfate, followed by filtration and removal of the pentane and ether at reduced pressure, afforded 916 mg (99.6% yield) of the isomerized aldehyde, whose structural identity was confirmed by NMR analysis (δ 9.45, singlet, CHO).

EXAMPLE VI

Preparation of 3-Methyl-5-(2,6,6-trimethyl-1-cyclohexen-1-yl)-1,3-pentadienylphosphonic acid, Diethyl Ester A solution of 508 mg (1.76 mmoles) of methylenebisphosphonic acid, tetraethyl ester, prepared as described in Example I, in 2.5 mL of benzene and 1.5 mL of anhydrous tetrahydrofuran (THF) was added dropwise slowly over 5 minutes to a stirred mixture of 69 mg (1.7 mmoles) of sodium hydride (60% dispersion in mineral oil, which was removed prior to the reaction by washing with hexane) and 1.0 mL of benzene, protected from atmospheric moisture and maintained at a temperature of 15°-20° C. by use of an external cold water bath. This mixture was stirred for an additional 15 minutes, after which a solution of 208 mg (1.01 mmole) of aldehyde (prepared as described in Example V) in 2.5 mL of benzene was added dropwise rapidly. After stirring this mixture at room temperature for 25 minutes, it was diluted with 20 mL of 1:1 (v/v) pentane:ether and washed in successive order with 7:3 (v/v) 1M aqueous sodium hydroxide:methyl alcohol (2×40 mL) to remove excess bisphosphonate and then with saturated brine (20 mL). The organic layer was then dried over anhydrous magnesium sulfate and subsequently filtered. Removal of the pentane, ether, and benzene by evaporation at reduced pressure afforded 320 mg (93% yield) of the desired vinyl phosphonate.

EXAMPLE VII

Preparation of 3-Methyl-5-(2,6,6-trimethyl-1-cyclohexen-1-yl)-1,3-pentadienylphosphonic Acid, Diisopropyl Ester The ylide was prepared in the manner described in the procedure of Example VI by reaction of 605 mg (1.76 mmoles) of methylenebisphosphonic acid, tetraisopropyl ester (produced in accordance with Example II), with 69 mg (1.7 mmoles) of 60% sodium hydride. Subsequent addition of 195 mg (0.95 mmole) of the unsaturated aldehyde produced in accordance with Example V and stirring of the mixture at 20° C. for 25 minutes completed the reaction. The product was isolated after dilution of the mixture with 20 mL of 1:1 (v/v) pentane:ether and washing in successive order with 1:1 (v/v) 1M aqueous sodium hydroxide:methyl alcohol (2×40 mL) to remove excess bisphosphonate and then with saturated brine (20 mL). The organic layer was then dried over anhydrous magnesium sulfate and subsequently filtered. Removal of the pentane, ether, and benzene by evaporation at reduced pressure afforded 313 mg (90% yield) of the desired vinyl phosphonate.

EXAMPLE VIII

Preparation of 3-Methyl-5-(2,6,6-trimethyl-1-cyclohexen-1-yl)-1,4-pentadienylphosphonic Acid, Diethyl Ester The reaction was conducted in the manner described in the procedure of Example VI using the following reagents: 2.96 g (10.25 mmoles) of methylenebisphosphonic acid, tetraethyl ester (produced in accordance with Example I), in 20 mL of 3:2 (v/v) benzene:anhydrous tetrahydrofuran; 413 mg (10.3 mmoles) of 60% sodium hydride in 8.0 mL of benzene; and 1.204 g (5.85 mmoles) of unsaturated aldehyde (produced in accordance with Example IV) in 12.0 mL of benzene. Isolation of the product as described in the procedure of Example VI afforded 1.901 g (95.5% yield) of the desired vinyl phosphonate.

EXAMPLE IX

Preparation of 3-Methyl-5-(2,6,6-trimethyl-1-cyclohexen-1-yl)-1,4-pentadienylphosphonic Acid, Diisopropyl Ester The reaction was conducted in the manner described in the procedure of Example VII using the following reagents: 303 mg (0.88 mmole) if methylenebisphosphonic acid, tetraisopropyl ester (produced in accordance with Example II), in 2.5 mL of 3:2 (v/v) benzene:anhydrous tetrahydrofuran; 36 mg (0.90 mmole) of 60% sodium hydride in 1.0 mL of benzene; and 98 mg (0.47 mmole) of unsaturated aldehyde (produced in accordance with Example IV) in 1.5 mL of benzene. Isolation of the product as described in the procedure of Example VII afforded 104 mg (60% yield) of the desired vinyl phosphonate.

EXAMPLE X

Preparation of 3-Methyl-5-(2,6,6-trimethyl-1-cyclohexen-1-yl)-2,4-pentadienylphosphonic Acid, Diethyl Ester A mixture of the vinyl phosphonate produced in accordance with Example VIII (943 mg, 2.77 mmoles) and 99 mg (0.88 mmoles) of potassium tert-butoxide in 12 mL of anhydrous dimethyl sulfoxide (DMSO) was stirred, protected from atmospheric moisture, at 20° C. for 80 minutes. The product was isolated by dilution of the reaction mixture with 100 mL of ether and subsequent washing with 120 mL portions of 10% aqueous sodium chloride (4×120 mL). The organic layer was then dried over anhydrous magnesium sulfate and filtered. Removal of the ether by evaporation at reduced pressure afforded 718 mg (76% yield) of the desired allylic phosphonate, whose structural integrity was confirmed by NMR analysis [δ 2.75, doublet of doublets, J=8 Hz and 22 Hz, CH$_2$P]. In a similar manner, this allylic phosphonate could be prepared by isomerization of 3-methyl-5-(2,6,6-trimethyl-1-cyclohexen-1-yl)-1,3-pentadienylphosphonic acid, diethyl ester, produced in accordance with Example VI.

EXAMPLE XI

Preparation of 3-Methyl-5-(2,6,6-trimethyl-1-cyclohexen-1-yl)-2,4-pentadienylphosphonic Acid, Diisopropyl Ester A mixture of vinyl phosphonate produced in accordance with Example VII (308 mg, 0.84 mmole) and 88 mg. (0.78 mmole) of potassium tert-butoxide in 4 mL of anhydrous dimethyl sulfoxide was stirred, protected from atmospheric moisture, at 20° C. for 30 minutes. Isolation of the product in the manner described in the procedure of Example X afforded 238 mg (77% yield) of the desired allylic phosphonate. This latter compound could also be prepared by isomerization of 3-methyl-5-(2,6,6-trimethyl-1-cyclohexen-1-yl)-1,4-pentadienylphosphonic acid, diisopropyl ester, produced in accordance with Example IX.

EXAMPLE XII

Preparation of 2-Butenyl-1,4-bisphosphonic Acid, Tetraethyl Ester

A solution of 2.00 mL (18.9 mmoles) of trans-1,4-dichloro-2-butene in 3.00 mL (17.5 mmoles) of triethyl phosphite was added dropwise slowly over 25 minutes to a flask containing 5.00 mL (29.2 mmoles) of triethyl phosphite, maintained at a temperature of approximately 140° C. (external oil bath temperature). This mixture was subsequently heated at 140° C. for an additional 12 hours, during which time ethyl chloride was continuously distilled out of the reaction flask. At that point, the external oil bath temperature was raised to 180° C. to distill over as much of the remaining triethyl phosphite as possible. The desired product was then obtained by fractional distillation under reduced pressure, affording 5.40 g (87.5% yield) of bisphosphonate: bp 161°-184° C. (bath temperature, 0.25 mm).

EXAMPLE XIII

Preparation of 1,1,8,8-Tetramethoxy-2,7-dimethyl-2,4,6-octatriene

To a solution of 312 mg (0.95 mmole) of 2-butenyl-1,4-bisphosphonic acid, tetraethyl ester (produced in accordance with Example XII), and 0.25 mL (2.07 mmoles) of pyruvic aldehyde dimethyl acetal (available from Aldrich Chemical Co.) in 3.25 mL of 12:1 (v/v) anhydrous tetrahydrofuran:dimethyl sulfoxide, protected from atmospheric moisture and maintained at a temperature of approximately 5° C. by use of an external ice water bath, was added 211 mg (1.88 mmoles) of potassium tert-butoxide. This mixture was subsequently stirred in the cold for 15 minutes and then at room temperature for 7 hours. The product was isolated by dilution of the mixture with 30 mL of 1:1 (v/v) ether:pentane and subsequent washing of the organic layer with 10% aqueous sodium chloride (3×30 ml). The organic layer was then dried over anhydrous sodium sulfate and filtered. Removal of the volatile organic solvents by evaporation at reduced pressure afforded 151 mg (62% yield) of bisacetal.

EXAMPLE XIV

Preparation of 2,7-Dimethyl-2,4,6-octatrienedial

A solution of 150 mg (0.585 mmole) of 1,1,8,8-tetramethoxy-2,7-dimethyl-2,4,6-octatriene, produced in accordance with Example XIII, in 3.5 mL of 4:2:1 (v/v/v) glacial acetic acid:tetrahydrofuran:water was heated at 45° C. (external oil bath temperature) for 3 hours. After cooling the solution to room temperature, the product was isolated by dilution of the mixture with 25 mL of 4:1 (v/v) ether:dichloromethane and washing the organic layer in successive order with saturated brine (2×25 mL); 4:1 (v/v) saturated brine:1M aqueous sodium hydroxide (2×25 mL), and saturated brine (25 mL). The organic layer was then dried over anhydrous magnesium sulfate and filtered. Removal of the volatile organic solvents by evaporation at reduced pressure afforded 86 mg (90% yield) of the desired bisaldehyde, previously prepared in a similar manner by H. Pommer, et al., *Angew. Chem.*, 72, 911 (1960).

EXAMPLE XV

Preparation of Beta-Carotene

To a solution of 192 mg (0.564 mmole) of 3-methyl-5-(2,6,6-trimethyl-1-cyclohexen-1-yl)-2,4-pentadienylphosphonic acid, diethyl ester (produced in accordance with Example X) and 41 mg (0.25 mmole) of 2,7-dimethyl-2,4,6-octatrienedial (produced in accordance with Example XIV) in 2.25 mL of 8:1 (v/v) anhydrous tetrahydrofuran:dimethyl sulfoxide, protected from atmospheric moisture and maintained at a temperature of approximately 5° C. by use of an external ice water bath, was added 59 mg (0.526 mmole) of potassium tert-butoxide. This mixture was subsequently stirred in the cold for 15 minutes and then at room temperature for 3.5 hours. The product was isolated by dilution of the mixture with 25 mL of 4:1 (v/v) ether:dichloromethane and subsequent washing of the organic layer with 25 mL portions of 10% aqueous sodium chloride (3×25 mL). The organic layer was then dried over anhydrous magnesium sulfate and filtered. Removal of the volatile organic solvents by evaporation at reduced pressure, followed by filtration through a small column of silica gel (10 mL, 60–200 mesh, elution with 40 mL of 3:1 (v/v) hexane:benzene) to remove any unreacted starting materials afforded 82 mg (61% yield) of deep-purple crystals, identified by NMR analysis as beat-carotene: mp 183°-185° C.

EXAMPLE XVI

Preparation of all-trans Retinoic Acid, Ethyl Ester

To a solution of 57 mg (0.40 mmole) of ethyl 3-methyl-4-oxobutenoate [prepared according to a procedure described by R. W. Curley, Jr., et al., *J. Org. Chem.*, 51, 256 (1986); an alternate synthesis has been described by A. Guingant, et al., *J. Org. Chem.*, 52, 4788 (1987); the compound is commercially available from Fluka Chemical Corp., Ron Kon Koma, New York 11779.] and 132 mg (0.388 mmole) of 3-methyl-5-(2,6,6-trimethyl-1-cyclohexen-1-yl)-2,4-pentadienylphosphonic acid diethyl ester (produced in accordance with Example X) in 3.5 mL of 6:1 (v/v) anhydrous tetrahydrofuran:dimethyl sulfoxide, protected from atmospheric moisture and maintained at a temperature of approximately 5° C. by use of an ice water bath, was added 43 mg (0.38 mmole) of potassium tert-butoxide. This mixture was subsequently stirred in the cold for 10 minutes and then at room temperature for 6 hours. The product was isolated by dilution of the mixture with 30 mL of 1:1 (v/v) pentane:ether and subsequent washing of the organic layer with 30 mL portions of 10% aqueous sodium chloride (3×30 mL). The organic layer was then dried over anhydrous magnesium sulfate and filtered. Removal of the volatile organic solvents by evaporation at reduced pressure, followed by filtration through a small column of silica gel (15 mL, 60–200 mesh, elution with 75 mL of hexane-4% ether) to remove any unreacted starting materials, afforded 76 mg (61% yield) of ethyl retinoate shown by high-field (300 MHz) NMR analysis to be predominantly the all trans stereoisomer. The product was characterized by three broad singlets of equal intensity at δ 2.37, 2.02, and 1.73 (3 vinyl methyls). For tables listing spectroscopic properties of retinoids, see: R. S. H. Liu, et al. *Tetrahedron*, 40, 1931–1969 (1984). Ethyl retinoate was also prepared in a similar manner from ethyl 3-methyl-4-oxo-butenoate and 3-methyl-5-(2,6,6-trimethyl-1-cyclohexen-1-yl)-2,4-pentadienylphosphonic acid diisopropyl ester (produced in accordance with Example XI).

EXAMPLE XVII

Preparation of 13-cis-Retinoic Acid

To a solution of 88 mg (0.258 mmole) of 3-methyl-5-(2,6,6-trimethyl-1-cyclohexen-1-yl)-2,4-pentadienyl-phosphonic acid diethyl ester (produced in accordance with Example X) and 37 mg (0.324 mmole) of 5-hydroxy-4-methyl-2-(5H) furanone [prepared according to a procedure described by G. Pattenden, et al., *J. Chem. Soc.* (C), 1984 (1968). An alternate synthesis has been described by C. G. Wermuth, et al., *J. Org. Chem.*, 46, 4889 (1981).] in 2.25 mL of 8:1 (v/v) anhydrous tetrahydrofuran:dimethyl sulfoxide, protected from atmospheric moisture and maintained at a temperature of approximately 5° C. by use of an ice water bath, was added 64 mg (0.57 mmole) of potassium tert-butoxide. This mixture was subsequently stirred in the cold for 15 minutes and then at room temperature for 3.5 hours. After acidifying the mixture by addition of 0.50 mL of 2M aqueous hydrochloric acid, it was diluted with 25 mL of 4:1 (v/v) ether:dichloromethane. The organic layer was washed in successive order with 10% aqueous sodium chloride (2×25 mL), water (1×25 mL), and saturated brine (1×25 mL), dried over anhydrous magnesium sulfate, and filtered. Removal of the volatile organic solvents by evaporation at reduced pressure, followed by filtration through a small column of silica gel (6 mL, 40–140 mesh, elution with 25 mL of pentane-20% ether) to remove any unreacted phosphonate afforded 44 mg (57% yield) of orange crystals, shown by NMR analysis (in CDCl$_3$ solution) to be a mixture of stereoisomers. The predominate stereoisomer (comprising approximately 75–80% of the mixture) was characterized by a doublet (J=15 Hz) at δ 7.81 (vinyl hydrogen bonded to C-12), a broad singlet at δ 5.68 (vinyl hydrogen bonded to C-14), and a broad singlet at δ 2.11 (CH$_3$ bonded to C-13). By comparison with the NMR data reported (in "tau values", where "tau"=10−δ) for various stereoisomers of retinoic acid by Pattenden, et al., [*J. Chem. Soc., C.*, 1984–1997 (1968)], this major component was shown to be 13-cis-retinoic acid. The other (minor) component in the product exhibited broad singlets at δ 5.82 (vinyl hydrogen bonded to C-14) and δ 2.37 (CH$_3$ bonded to C-13), absorptions characteristic of all-trans retinoic acid.

Although the foregoing invention has been described in some detail by way of example, various changes and modifications to the specific procedures which have been illustrated may be practiced within the scope of the appended claims.

What is claimed is:

1. Phosphonates of the formula:

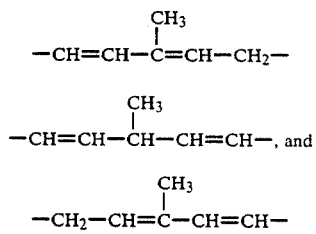

in which R is an alkyl group having up to four carbon atoms, and R$_1$ is a 3-methyl pentadienyl group.

2. The phosphonate of claim 1 wherein R$_1$ is selected from the group consisting of $$-CH=CH-\underset{\underset{CH_3}{|}}{C}=CH-CH_2-$$

$$-CH=CH-\underset{\underset{CH_3}{|}}{CH}-CH=CH-, \text{ and}$$

$$-CH_2-CH=\underset{\underset{CH_3}{|}}{C}-CH=CH-$$

3. The phosphonate of claim 1 which is 3-methyl-5-(2,6,6-trimethyl-1-cyclohexen-1-yl)-2,4-pentadienyl-phosphonic acid, diethyl ester.

4. The phosphonate of claim 1 which is 3-methyl-5-(2,6,6-trimethyl-1-cyclohexen-1-yl)-2,4-pentadienyl-phosphonic acid, diisopropyl ester.

5. The phosphonate of claim 1 which is 3-methyl-5-(2,6,6-trimethyl-1-cyclohexen-1-yl)-1,3-pentadienyl-phosphonic acid, diethyl ester.

6. The phosphonate of claim 1 which is 3-methyl-5-(2,6,6-trimethyl-1-cyclohexen-1-yl)-1,3-pentadienyl-phosphonic acid, diisopropyl ester.

7. The phosphonate of claim 1 which is 3-methyl-5-(2,6,6-trimethyl-1-cyclohexen-1-yl)-1,4-pentadienyl-phosphonic acid, diethyl ester.

8. The phosphonate of claim 1 which is 3-methyl-5-(2,6,6-trimethyl-1-cyclohexen-1-yl)-1,4-pentadienyl-phosphonic acid, diisopropyl ester.

* * * * *

REEXAMINATION CERTIFICATE (2036th)

United States Patent [19]

Babler

[11] B1 4,916,250

[45] Certificate Issued Jun. 8, 1993

[54] PHOSPHONATE REAGENT COMPOSITIONS

[75] Inventor: James H. Babler, Chicago, Ill.

[73] Assignee: Loyola University of Chicago, Chicago, Ill.

Reexamination Request:
No. 90/002,463, Oct. 4, 1991

Reexamination Certificate for:
Patent No.: 4,916,250
Issued: Apr. 10, 1990
Appl. No.: 264,543
Filed: Oct. 31, 1988

[51] Int. Cl.$^5$ .............................................. C07F 9/40
[52] U.S. Cl. ...................................... 558/217; 558/87; 558/88; 558/351; 560/128; 562/510
[58] Field of Search ......................................... 558/217

[56] References Cited

U.S. PATENT DOCUMENTS

| | | | |
|---|---|---|---|
| 3,600,473 | 8/1971 | Sarmatis | 558/217 |
| 4,175,204 | 11/1979 | Babler | 560/262 |
| 4,595,793 | 6/1986 | Vogel et al. | 558/217 X |

OTHER PUBLICATIONS

Bourguignon, J. J. and C. G. Wermuth, "Lactone Chemistry. Synthesis of Beta-Substituted, Gamma-Functionalized Butanolides and Butenolides and Succinaldehydic Acids from Glyoxylic Acid", *J. Org. Chem.* (1981), 46, pp. 4889-4894.

Czekanski, T., H. Gross and B. Contisella, "Methandisphosphonsaureester durch UV-Induzierte Michaelis-Becker-Reaktion", 35, *J. f. prakt. Chemie.* Band 324, Heft 4, (1982), pp. 537-544.

Curley, R. W., Jr. and C. J. Ticoras, "Stereospecific Synthesis of the Important Retinoid Synthon Ethyl trans-3-Formyl-2-butenoate via Direct Two-Stage Oxidation of Ethyl 3-Methyl-2-butenoate", *J. Org. Chem.* (1986), 51, pp. 256-258.

Isler, O., W. Huber, A. Ronco and M. Kofler, "Synthese des Vitamin A", *Helv. Chim. Acta,* 30, 1947, vol. XXX, pp. 1911-1927.

Julia, M. and D. Arnould, "Synthese a l'aide de Sulfones, III Syntheses de la vitamine A", *Bull. Soc. Chim. Fr.* (1973), Part 2, pp. 746-750.

Laugraud, S., A. Guingant and J. d'Angelo, "A Direct Route for the Synthesis of (E)-3-Alkyl-4-oxo-2-butenoic Acid Esters", *J. Org. Chem.* (1987), 52, pp. 4788-4790.

Liu, R. S. H. and A. E. Asato, Tetrahedron Report No. 165, "Photochemistry and Synthesis of Stereoisomers of Vitamin A", *Tetrahedron,* vol. 40, No. 11, (1984), pp. 1931-1969.

Pattenden, G. and B. C. L. Weedon, "Carotenoids and Related Compounds. Part XVIII, Synthesis of cis and D-cis-Polyenes by Reactions of the Wittig Type", *J. Chem. Soc.* (C) (1968), pp. 1984-1997.

Pommer, H. and R. Kuhn, "Synthesen in der Carotinoid-Reihe", *Angew. Chem.*, 72 (1960), No. 23, pp. 911-915.

Rammamurthy, V., G. Tustin, C. C. Yau and R. S. H. Liu, "Preparation of Sterically Hindered Geometric Isomers of 7-Cis-Beta-Ionyl and Beta-Ionylidene Derivatives in the Vitamin A Series", *Tetrahedron,* vol. 31 (1975), pp. 193-199.

Reif, W. and H. Grassner, "Die Technische Vitamin-A-Synthese der BASF", *Chemie-Ing.-Techn.,* 45, (1973)m No. 10a, pp. 646-652.

Rosenberger, M., W. Jackson and G. Saucy, "The Synthesis of Beta, Gama and Alpha, Beta-Unsaturated Aldehydes via Polyene Epoxides", *Helvetica Chimica Acta,* vol. 63, Fasc. 6 (1980), No. 175, pp. 1665-1674.

Surmatis, J. D. and R. Thommen, "The Synthesis of Trans-Beta-Carotene from Retinyl Phosphonate by the Michaelis-Arbuzov Reaction", *J. Org. Chem.*, vol. 34, No. 3, (1969), pp. 559-560.

Freyschlag et al., *Angewandte Chemie,* 77:277-282 (1965).

Freyschlag et al., *Angew. Chem. Internat. Edit,* 4:287-291 (1965).

Morrison & Boyd, "Organic Chemistry", 4th Ed., (1983), pp. 424-426.

Solomens, "Organic Chemistry", 5th Ed., (Date not known), pp. 476 and 495.

Gutsche & Pasto, "Fundamentals of Organic Chemistry", (1975), pp. 105-109.
Jacoby et al.; *Synthesis*, (1990), pp. 301-304.

*Primary Examiner*—Joseph Paul Brust
*Agent, Attorney, or Firm*—Marshall, O'Toole, Gerstein, Murray & Borun

[57] ABSTRACT

Novel phosphonate compounds of the formula

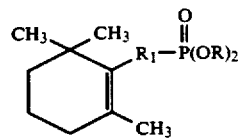

are disclosed and claimed, as well as methods for manufacturing the phosphonates from C-14 through C-16 aldehydes. The phosphonate compounds of the present invention can be employed to form 13-cis retinoic acid, retin-A and beta-carotene.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 5-8 is confirmed.

Claims 1-4 are cancelled.

New claim 9 is added and determined to be patentable.

9. *Phosphonates of the formula:*

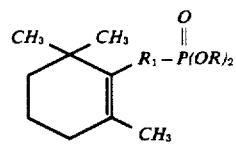

*in which R is an alkyl group having up to four carbon atoms, and $R_1$ is selected from the group consisting of*

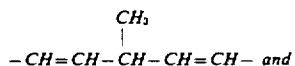

* * * * *